United States Patent [19]

Rhodes

[11] Patent Number: 5,277,893
[45] Date of Patent: Jan. 11, 1994

[54] DIRECT RADIOLABELING OF SUBSTRATES CONTAINING MONOSULFIDES OR DISULFIDE BONDS WITH RADIONUCLIDES

[75] Inventor: Buck A. Rhodes, Albuquerque, N. Mex.

[73] Assignee: RhoMed, Incorporated, Albuquerque, N. Mex.

[21] Appl. No.: 864,470

[22] Filed: Apr. 6, 1992

Related U.S. Application Data

[63] Continuation of Ser. No. 565,275, Aug. 8, 1990, Pat. No. 5,102,990, which is a continuation-in-part of Ser. No. 391,474, Aug. 9, 1989, Pat. No. 5,078,985.

[51] Int. Cl.$^5$ .................. A61K 49/02; A61K 43/00
[52] U.S. Cl. .................. 424/1.49; 530/391.5; 530/402; 534/14; 424/1.69
[58] Field of Search ............ 424/1.1; 530/391.3, 530/391.5, 402

[56] References Cited

U.S. PATENT DOCUMENTS

| | | | |
|---|---|---|---|
| 3,812,264 | 5/1974 | Nouel | 424/1.1 |
| 4,305,922 | 12/1981 | Rhodes | 424/1.1 |
| 4,311,688 | 1/1982 | Burchiel et al. | 424/1.1 |
| 4,323,546 | 4/1982 | Crockford et al. | 424/1.1 |
| 4,331,647 | 5/1982 | Goldenberg | 424/1.1 |
| 4,348,376 | 9/1982 | Goldenberg | 424/1.1 |
| 4,421,735 | 12/1983 | Haber et al. | 424/1.1 |
| 4,424,200 | 1/1984 | Crockford et al. | 424/1.1 |
| 4,427,646 | 1/1984 | Olexa et al. | 424/1.1 |
| 4,472,371 | 9/1984 | Burchiel et al. | 424/1.1 |
| 4,478,815 | 10/1984 | Burchiel et al. | 424/1.1 |
| 4,479,930 | 10/1984 | Hnatowich | 424/1.1 |
| 4,622,240 | 11/1986 | Meares et al. | 562/443 |

(List continued on next page.)

FOREIGN PATENT DOCUMENTS

| | | |
|---|---|---|
| 2016235 | 11/1990 | Canada . |
| 0237150 | 9/1987 | European Pat. Off. ...... A61K 49/02 |
| 271806 | 6/1988 | European Pat. Off. . |
| 0336678 | 4/1989 | European Pat. Off. ...... A61K 49/02 |

(List continued on next page.)

OTHER PUBLICATIONS

"The Labeling of High Affinity Sites of Antibodies with 99mTc," by Chang H. Paik et al., Int. J. Nucl. Med. Biol., vol. 12, No. 1, pp. 3–8 (1985).

"Antibodies Labeled with $^{199}$Au: Potential for $^{199}$Au: for Radioimmunotherapy," by Anderson, P., et al., Nucl. Med. Biol., vol. 15, No. 3, pp. 293–297, (1988).

"Engineered Metal-Binding Proteins: Purification to Protein Folding," by Arnold, Frances H., et al., Science, vol. 252, pp. 1796–1797 (Jun. 28, 1991).

"Laminin Receptor Complementary DNA-deduced Synthetic Peptide Inhibits Cancer Cell Attachment to Endothelium," by Castronovo, Vincent, et al., Cancer Research, vol. 51, pp. 5672–5678 (Oct. 15, 1991).

"Increased Expression of the Laminin Receptor in Human Colon Cancer," by Cioce, Vittoria, et al., Articles, Journal of National Cancer Institute, vol. 83, No. 1, pp. 29–36 (Jan. 2, 1991).

"Requirements for a Treatment Planning System for Radioimmunotherapy," by DeNardo, G. L., et al., Int.

(List continued on next page.)

Primary Examiner—Robert L. Stoll
Assistant Examiner—John M. Covert
Attorney, Agent, or Firm—Deborah A. Peacock; Donovan F. Duggan

[57] ABSTRACT

Proteins containing one or more disulfide bonds are radiolabeled with radionuclides of technetium or rhenium for use in diagnosis and treatment of a variety of pathologic conditions. Radiolabeling is accomplished by partial reduction of the disulfide bonds of the protein using Sn (II), or using other reducing agents followed by the addition of Sn (II), removal of excess reducing agent and reduction by-products, and addition of a specified amount of pertechnetate or perrhenate reducing agent, such as stannous tartrate, with the addition accomplished in such a manner that further reduction of the protein is limited. The resulting product may be stored frozen or lyophilized, with radiolabeling accomplished by the addition of pertechnetate or perrhenate solution.

32 Claims, No Drawings

U.S. PATENT DOCUMENTS

| | | |
|---|---|---|
| 4,647,445 | 3/1987 | Lees .................. 424/1.1 |
| 4,652,440 | 3/1987 | Paik et al. ............. 424/1.1 |
| 4,668,503 | 5/1198 | Hnatowich ............ 424/1.1 |
| 4,670,545 | 6/1987 | Fritzberg et al. ........ 534/14 |
| 4,732,864 | 3/1988 | Tolman ................ 436/547 |
| 4,810,693 | 3/1989 | Pickart ................ 514/18 |
| 4,877,868 | 10/1989 | Reno et al. ............ 424/1.1 X |
| 4,917,878 | 4/1990 | Thakur ................ 424/1.1 |
| 4,986,979 | 1/1991 | Morgan, Jr. et al. .... 424/1.1 |

(List continued on next page.)

FOREIGN PATENT DOCUMENTS

| | | | |
|---|---|---|---|
| 2043459 | 5/1969 | France .............. | A61K 27/00 |
| 85/03231 | 8/1985 | PCT Int'l Appl. ....... | A61K 49/02 |
| 87/04164 | 7/1987 | PCT Int'l Appl. ....... | A61K 49/02 |
| 88/07382 | 10/1988 | PCT Int'l Appl. ....... | A61K 49/02 |

OTHER PUBLICATIONS

J. Radiol. Oncology Biol. Phys., vol. 11, pp. 335–348, (1985).

"Copper-67-Labeled Monoclonal Antibody Lym-1, A Potential Radiopharmaceutical for Cancer Therapy: Labeling and Biodistribution in RAJI Tumored Mice," by Deshpande, S. V., et al., J. Nucl. Med., vol. 29, No. 2, pp. 217–225, (Feb. 1988).

"Imaging Focal Sites of Bacterial Infection in Rats with Indium-111-Labeled Chemotactic Peptide Analogs," by Fischman, Alan J., et al., Journal of Nucl. Med., vol. 32, No. 3, pp. 483–491 (Mar. 1991).

"Peptide Architecture, Design of Stable α-Helical Metallopeptides via a Novel Exchange-Inert $Ru^{III}$ Complex," by Ghadiri, M. Reza, et al., J. Am. Chem. Soc., vol. 112, No. 26, pp. 9633–9635 (1990).

"Gallium Radiopharmaceutical Chemistry," by Green, M. A., et al., Review, Nucl. Med. Biol., vol. 16, No. 5, pp. 435–448, (1989).

"Radioactive Gold Cluster Immunoconjugates: Potential Agents for Cancer Therapy," by Hainfeld, James F., et al., Nucl. Med. Biol., vol. 17, No. 3, pp. 287–294, (1990).

"Integrins: A Family of Cell Surface Receptors," by Hynes, Richard O., Review, Cell, vol. 48, pp. 549–554 (1987).

"Metalloantibodies," by Iverson, Brent L., et al., Reports, Science, vol. 249, pp. 659–662 (Aug. 1990).

"Autoradiographic analysis of formylpeptide chemoattractant binding, uptake and intracellular processing by neutrophils," by Janeczek, Amelia H., et al., Journal of Cell Science, vol. 94, pp. 155–168 (1989).

"Radioiodinated Somatostatin Analog Scintigraphy in Small-Cell Lung Cancer," by Kwekkeboom, Dirk J., et al., Journal of Nucl. Med., vol. 32, No. 10, pp. 1845–1848 (Oct. 1991).

"The Biodistribution of Radiocopper-Labeled Compounds," by Mercer-Smith, Janet A., et al., Copper Bioavailability and Metabolism, C. Kies, Ed., pp. 103–121, (1990).

"The Use of Monoclonal Antibody Conjugates for the Diagnosis and Treatment of Cancer," by Pietersz, G. A. et al., Special Invited Article, Immunology and Cell Biology, vol. 65, Pt. 2, pp. 111–125, (1987).

"Preparation and Characterization of Copper-67 Porphyrin-Antibody Conjugates," by Roberts, Jeanette C., et al., J. Immunol. Meth., vol. 105, pp. 153–164, (1987).

"Labeling Antibodies with Copper Radionuclides Using N-4-Nitrobenzyl-5-(4-carboxyphynyl)-10,15,-20-tris(4-sulfophenyl) Porphine," by Roberts, Jeanette, C., et al., Appl. Radiat. Isot., vol. 40, No. 9, pp. 775–781, (1989).

"Technetium-99, and 99m chelates with N-donor ligands: a new class of potential cationic radiopharmaceuticals," by Seifert, S., et al., Technitium in Chemistry and Nuclear Medicine, E. Deutsch, M. Nicolini, H. N. Wagner, Jr., eds., Cortina International, Verona, pp. 19–23 (1983).

"Laminin receptor on platelets is the integrin VLA-6," by Sonnenberg, Arnoud, et al., Nature, vol. 336, pp. 487–489 (Dec. 1988).

"Interaction of human platelets with laminin and identification of the 67 kDa laminin receptor on platelets," by Tandon, Narendra N., et al., Biochem. J., vol. 274, pp. 535–542 (1991).

"Identification of an amino acid sequence in the laminin A chain mediating mast cell attachment and spreading," by Thompson, H. L., et al., Immunol., vol. 72, pp. 144–149 (1991).

"Zinc Coordination, Function, and Structure of Zinc Enzymes and Other Proteins," by Vallee, Bert L., et al., Biochemistry, vol. 29, No. 24, pp. 5647–5659 (Jun. 19, 1990).

(List continued on next page.)

U.S. PATENT DOCUMENTS

| | | | |
|---|---|---|---|
| 5,011,676 | 4/1991 | Thakur | 424/1.1 |
| 5,023,237 | 6/1991 | Pickart | 514/18 |
| 5,053,493 | 10/1991 | Pak et al. | 530/402 |
| 5,059,588 | 10/1991 | Pickart | 514/12 |
| 5,061,641 | 10/1991 | Shochat et al. | 436/545 |
| 5,078,985 | 1/1992 | Rhodes | 424/1.1 |
| 5,102,990 | 4/1992 | Rhodes | 424/1.1 X |
| 5,116,596 | 5/1992 | Bremer et al. | 424/1.1 |
| 5,128,119 | 7/1992 | Griffiths | 424/1.1 |

OTHER PUBLICATIONS

"Three Approaches to Radiolabeling Antibodies with 99mTc" by W. C. Eckelman et al., *Nucl. Med. Biol.*, vol. 16, No. 2, pp. 171–176 (1989).

"A New Method for Protein Labeling with 99mTc" by D. Blok et al., *Nucl. Med Biol.*, vol. 16, No. 1, pp. 11–16 (1989).

"Covalent Attachment of Chelating Groups to Macromolecules" by Gary E. Krejcarek, *Biochem. & Biophy. Res. Comm.*, vol. 77, No. 2, pp. 581–585 (1977).

"Biofunctional Chelating Agents for Binding Metal Ions to Proteins" by T. G. Wensel et al., S. W. Burchiel and B. A. Rhodes, Eds., *Radioimmunoimaging and Radioimmunotherapy*, pp. 185–196 (1983).

"99mTc Labeling of Proteins: Initial Evaluation of a Novel Diaminedithiol Bifunctional Chelating Agent" by K. E. Baidoo, *Cancer Res. (Supp)*, vol. 50, pp. 799s–803s (Feb. 1990).

"Radioimmunoimaging of Experimental Thrombi in Dogs Using Technetium-99-m-Labeled Monoclonal Antibody Fragments Reactive with Human Platelets" by P. Som et al., *J. Nucl. Med.*, vol. 27, No. 8, pp. 1315–1320 (Aug. 1986).

"Technetium-99m—Albumin" by H. S. Stern et al., Book chapter published by Johns Hopkins Medical Institutions, Baltimore, Md., pp. 359–375 (U.S. Atomic Energy Commission) (1966).

"Use of Fe(II) or Sn(II) Alone for Technitium Labeling of Albumin" by M. S. Lin et al., *J. Nucl. Med.*, vol. 12, pp. 204–211 (1971).

"99m Tc–Human Serum Albumin" by W. C. Eckelman et al., *J. Nucl. Med.*, vol. 12, pp. 707–710 (1971).

"A Rapid Chemical Method of Labeling Human Plasma Proteins with 99m Tc-Pertechnetate at pH 7.4" by D. W. Wong et al., *Journal of App. Radiation and Isotopes*, vol. 29, pp. 251–253.

"A Rapid Method for Labeling IgG with 99m" by L. G. Colombetti et al., Abstract from *J. Nucl. Med.*, Proceedings of 26th Annual Meeting, p. 652 (1979).

"A Novel Approach to Tc-99m-Labeled Monoclonal Antibodies" by A. Schwarz et al., Abstact from *J. Nucl. Med.*, Poster Sessions, Proceedings of 34th Ann. Mtg., vol. 28, No. 4, p. 721 (No. 695), (Apr. 1987).

"A Rapid and Efficient Method for Labeling IgG Antibodies with Tc-99m and Comparison to Tc-99m FAB' Antibody Fragments" by K. Y. Pak et al., Abstract from *J. Nucl. Med.*, Scientific Papers, Proceedings of the 36th Annual Meeting, vol. 30, No. 5, p. 793 (No. 268), (1989).

"Imaging of Inflammatory Arthritis with Technetium-99m-Labeled IgG" by F. Breedveld et al., *J. Nucl. Med.*, pp. 2017–2021 (1989).

"Coupling of the 99m Technetium-Nitrido Group to Monoclonal Antibody and Use of the Complexes for the Detection of Tumors in Mice" by J. Kanellos, *JNCI*, vol. 77, No. 2, pp. 431–439 (1986).

"Technetium-99m Labeling of Murine Monoclonal Antibody Fragments" by B. A. Rhodes et al., *J. Nucl. Med.*, vol. 27, No. 6, pp. 685–693 (May 1986).

"A Tc-99m Labelled Monoclonal Antibody, PR1A3, for Radioimmunoscintigraphy, RIS, of Colorectal Cancer" by M. Granowska, Abstract from *J. Nucl. Med.*, Proceedings of the 36th Annual Meeting, vol. 30, p. 748 (No. 80) (1989).

DIRECT RADIOLABELING OF SUBSTRATES CONTAINING MONOSULFIDES OR DISULFIDE BONDS WITH RADIONUCLIDES

CROSS-REFERENCE TO RELATED APPLICATION

This is a continuation of U.S. Pat. No. 5,102,990, Ser. No. 565,275, filed Aug. 8, 1990, entitled *Direct Radiolabeling of Antibodies and Other Proteins with Technetium or Phenium*, issued Apr. 7, 1992, which application is a continuation-in-part application of U.S. Pat. No. 5,078,985, issued Jan. 7, 1992, Ser. No. 391,474, filed Aug. 9, 1989, entitled *Radiolabeling Antibodies and Other Proteins with Technetium or Rhenium by Regulated Reduction*, the teachings of which are incorporated herein by reference.

BACKGROUND OF THE INVENTION

1. Field of the Invention (Technical Field)

This invention relates to a method, composition and kit for radiolabeling proteins, including antibodies, with radioisotopes of technetium and rhenium such as technetium-99m.

2. Description of the Related Art Including Information Disclosed under 37 C.F.R. Sections 1.97-1.99 (Background Art)

The use of radioisotopes to label proteins is well known. These compositions can be used in assays, can be administered to the human body to visualize or monitor functioning of various parts of the body or to determine the presence and location of particular antigens, antibodies, hormones and the like, and can be used in the treatment of various disease states. A variety of radioisotopes, including isotopes of iodine, technetium, indium, and rhenium have been used. It is also well known that protein molecules can be tagged or labeled with technetium-99m to form a diagnostic or imaging agent.

Technetium-99m has been utilized to radiolabel proteins, chelating agents, phosphonate bone scanning compositions and the like by a technique which utilizes sodium pertechnetate wherein the technetium initially is in the +7 state. Technetium-99m is generally available only as sodium pertechnetate. The pertechnetate must be contacted with a reducing agent, such as stannous chloride, in order to reduce the technetium to the +3, +4 or +5 oxidation state in the presence of the protein, chelating agent or like substance which is to be radiolabeled. The technetium must be maintained in this reduced state in order to maintain the chemical bond between the technetium molecule and the substrate being radiolabeled. It is also necessary that the technetium be firmly bound to the protein such that the reduced technetium is not transferred to other molecules or other proteins present in the assay, patient's blood or other media in which the radiolabeled substance will be utilized.

Several different methods have been utilized to radiolabel proteins, particularly monoclonal antibodies, with technetium-99m. The methods involve two general approaches. One approach is indirect in which a bifunctional chelating agent is attached to the protein via one functional group and the technetium-99m is attached via the other functional, or chelating, group. This method was introduced by Krejcarek, G. E. and Tucker, K. L. ("Covalent Attachment of Chelating Groups to Macromolecules," *Biochemical and Biophysical Research Communications* Vol. 77, pp. 581-585, 1977) and has been widely employed in many variations using a wide variety of bifunctional chelating agents such as described in the review of Wensel and Meares (Wensel, T. C., and Meares, C. F., "'Bifunctional' Chelating Agents for Binding Metal Ions to Proteins," *Radloimmunolmaging and Radiolmmunotherapy*, S. W. Burchiel and B. A. Rhodes, eds., Elsevier Publishing Co., New York, pp 185-196, 1983). Other methods are disclosed by Hnatowich, D. J., U.S. Pat. Nos. 4,668,503 and 4,479,930, by Haber, E., and Khaw, B. A., U.S. Pat. No. 4,421,735, by Fritzberg, A. R., and Kasina, S., U.S. Pat. No. 4,670,545 and by Baidoo, K. E., et al, "$^{99m}$Tc Labeling of Proteins: Initial Evaluation of Novel Diaminedithiol Bifunctional Chelating Agent," *Cancer Res* (Supp), Vol. 50, pp. 799s-803s, 1990. The bifunctional chelate methods all present significant limitations, including the complexity of the radiolabeling procedure, the time required to accomplish radiolabeling, and the introduction and presence of substances which may affect the protein.

The other general approach is direct labeling. Although several direct methods have been reported, the first direct method capable of providing a sufficiently strong bond between the protein and the technetium-99m for In vivo applications was the direct or pretinning method described in U.S. Pat. No. 4,424,200, entitled *Method for Radiolabeling Proteins with Technetium-99m*, to Crockford, D. R., and Rhodes, B. A. In this method, a single reduction solution, consisting of stannous [Sn (II)] chloride with tartrate and phthalate salts, is used. This solution serves to (1) reduce the protein, thereby exposing reactive sulfide groups, (2) protect the reactive sulfide groups of the reduced protein to prevent reformation of disulfide bonds, (3) reduce sodium pertechnetate, and (4) complex the reduced Tc-99m and transfer it to the sulfide binding sites of the reduced protein. With this method, many proteins can be successfully radiolabeled with technetium-99m. Several investigators have reported on the use of this method (Rhodes, B. A., et al, "Technetium-99m Labeling of Murine Monoclonal Antibody Fragments," *Journal of Nuclear Medicine*, Vol. 27, pp. 685-693, 1986; Som, P., et al, "Radioimmunoimaging of Experimental Thrombi in Dogs Using Technetium-99m-Labeled Monoclonal Antibody Fragments Reactive with Human Platelets," *Journal of Nuclear Medicine*, Vol. 27, No. 8, pp. 1315-1320, 1986).

Other early direct labeling methods were reported, but did not yield a stable Tc-protein bond. The reason for the instability of the Tc-protein bond in prior methods (Stern, H. S., et al., *Radioactive Pharmaceuticals*, U.S. Atomic Energy Commission (1966), Textbook, Chapter 19, pp. 359-375; Lin, M. S., et al., "Use of Fe (II) or Sn (II) Alone for Technetium Labeling of Albumin," *Journal of Nuclear Medicine*, Vol. 12, No. 5, pps. 204-211, 1970; Eckelman, W. C. , et al. , $^{99m}$Tc-Human Serum Albumin," *Journal of Nuclear Medicine*, Vol. 12, No. 11, pp. 707-710, 1971; Wong, D. W., et al., "A Rapid Chemical Method of Labeling Human Plasma Proteins with $^{99m}$Tc-Pertechnetate at pH 7.4," *International Journal of Applied Radiation and Isotopes*, Vol. 29, pp. 251-253, 1978; Colombetti, L. G., et al., "A Rapid Method for Labeling IgG with 99m-Tc," *Journal of Nuclear Medicine*, Vol. 20, p. 652, 1979; Rhodes, B. A., U.S. Pat. No. 4,305,922, *Labeling Proteins With 99m-Tc by Ligand Exchange*, was that the protein had not been reduced to provide reactive sulfide groups which are necessary for the formation of strong bonds between the protein and the reduced radionuclide.

Subsequently, a number of methods have been reported which employ variations on the method of U.S. Pat. No. 4,424,200. These variations generally involve one or more of the following:

(1) Disulfide reducing agents other than Sn (II), such as 2-mercaptoethanol, dithiothreitol and their analogs, are used to reduce the protein; (2) reactive sulfide group protecting agents other than Sn (II), such as Zn (II), are employed; (3) pertechnetate reducing agents other than Sn (II), such as dithiothreitol, are used; and (4) complexing agents other then tartrate, such as phosphonates, are used to bind the reduced technetium and transfer it to the sulfide groups of the protein.

These methods have generally not resulted in any improvement over the method of U.S. Pat. No. 4,424,200. None of the methods disclosed yield results comparable to those achieved with the method, composition and kit disclosed herein.

Schwarz, A., and Steinstruaber, A., "A Novel Approach to Tc-99m-Labeled Monoclonal Antibodies," *Journal of Nuclear Medicine*, Vol. 28, p. 721, 1987, and Bremer, K. H., et al., European Patent Office Application No. 0 271 806 A2 (filed Dec. 8, 1987), reduce the disulfide groups of the protein with monothiols, such as 2-mercaptoethanol or 2-mercaptoethylamine. Sn (II) is used to reduce the pertechnetate and the reduced technetium is complexed with phosphonates or pyrophosphates. This method requires two or more vials and multiple steps to achieve radiolabeling. The phosphonates used can give rise to radiocolloid impurities in the final product. In addition, the chemicals used to reduce the disulfide groups, such as 2-mercaptoethanol, are potentially toxic.

Reno, J. W., et al., U.S. Pat. No. 4,877,868 *Radionuellde Antibody Coupling* and European Patent Office Application No. 0 237 150 (filed Jan. 19, 1987), used dithiothreitol (DTT) to reduce the disulfide groups of the protein, then protect the reactive sulfides with Zn (II) or other sulfhydryl group derivatizing reagents. They use tartrate salts to complex and transfer the reduced radionuclide. This method uses potentially toxic chemicals, such as dithiothreitol, to reduce the antibody. It also requires multiple steps to radiolabel the protein.

Pak, K. Y., et al, "A Rapid and Efficient Method for Labeling IgG Antibodies with Tc-99m and Comparison to Tc-99m Fab' Antibody Fragments," *Journal of Nuclear Medicine*, Vol. 30, p. 793, 1989, and Patent Cooperation Treaty International Patent Application No. WO 88/07382 (filed Apr. 1, 1988), used dithiothreitol to reduce the antibodies. Tartrate or glucoheptonate salts and their analogs are added to complex and transfer the reduced radionuclides. This method also uses potentially toxic chemicals, and requires multiple steps to radiolabel.

Shochat, D., et al., European Patent Office Application No. 0 336 678 (filed Apr. 3, 1989) use conventional disulfide reducing agents, such as cysteine, dithiothreitol, 2-mercaptoethanol, dithionite or or the like. They claim that the pretinning method of U.S. Pat. No. 4,424,200 does not work well, indicating that some of the radiometal is bound to sites which are comparatively labile in the presence of blood or other bodily fluids or tissues. They give a single example in the application, preparation of Tc-99m-anti-CEA-Fab', which example appears to be exactly that of the '200 patent. The use of Sn (II) to reduce sodium pertechnetate is well known in the prior art, and is disclosed in the '200 patent and other references.

The advantage of the Sn (II) method of reducing disulfides of proteins over other methods is that the Sn (II) both reduces the bond and complexes with the sulfide formed by the reduction to protect the sulfide from reverting to unreactive disulfide. When organic reducing agents such as DTT are used to reduce the disulfide groups of the protein, the reducing agent must be removed before sulfide protecting groups are added, otherwise the protecting groups will react, usually by formation of a precipitate, with the reducing agent. If the reducing agent is first removed to avoid this reaction between it and the sulfide protecting agent, then the reduced protein is left for a period of time in which the reactive sulfide groups can reform unreactive disulfide bonds. The Sn (II) reduction method, described in this invention, is new in that it permits simultaneous reduction and complexing of disulfides.

Other methods of direct labeling have also been reported which differ chemically from the four-step process described above. Paik, C. H., et al., U.S. Pat. No. 4,652,440, *Method of Stably Radiolabeling Antibodies with Technetium and Rhenium*, label proteins by Sn (II) reduction in the presence of a strong chelating agent, DTPA, which competes for the reduced radionuclide. Only strongly bonded Tc-99m labeling of the protein occurs probably by binding to native free sulfhydryl groups of the protein. however, considerable amounts of Tc-99m-DTPA is also formed and must be removed before the labeled protein can be used. This method lacks the first step of reducing the disulfide bonds needed to achieve high yields of strongly bonded radionuclide.

Sundrehagen, E., Patent Cooperation Treaty International Patent Application No. WO 85/03231 (filed Jan. 18, 1985), used gentisic acid to stabilize the low concentrations of Sn (II) used to reduce the pertechnetate. This method is useful in minimizing radiochemical impurities such as radiocolloids and oxidized radionuclide. This method lacks the first step of reducing the disulfide bonds needed to achieve high yields of strongly bonded radionuclide.

Lees, R. S., U.S. Pat. No. 4,647,445, *Radiolabelled Lipoproteins and Method for Making Same* uses dithionite at pH 8 to 9 to reduce both pertechnetate and lipoproteins simultaneously. This method requires that the labeled product be purified by column chromatography to remove radionuclidic impurities prior to use.

Breedveld, F. C., et al., "Imaging of Inflammatory Arthritis with Technetium-99m-Labeled IgG," *Journal of Nuclear Medicine*, Vol. 30, No. 12, pp. 2017-2021, 1989, first reduce pertechnetate with hydrochloric acid and then extract, transfer, and reduce the radionuclide to dryness. The protein is added to the vessel containing the dry, reduced radionuclide. Labeling is achieved during a 60 minute incubation at 40° C. This method requires extensive preprocessing of the radionuclide and is thus not readily applied to an instant kit process for labeling and formulating a drug.

McKenzie, I., et al., "Coupling of the $^{99m}$Technetium-Nitrido Group to Monoclonal Antibody and Use of the Complexes for the Detection of Tumors in Mice," *Journal of the National Cancer Institute*, Vol. 77, pp. 431-439, 1986, and Patent Cooperation Treaty Patent Application No. WO 87/04164 (filed Jan. 6, 1987), reduce antibodies to provide free sulfhydryl group binding sites or introduce free sulfhydryl groups binding sites and label the sites with $^{99m}TcN(Cl)_4^-$. The product requires purification by gel chromatography to remove radiochemical impurities prior to use.

All previous methods are limited because they fail to provide a one-step labeling kit and method which yields, within 15 minutes, an injectable product free of significant radiochemical impurities and a product in which the radionuclide is quantitatively and strongly bonded to the protein without altering immunoreactivity when the protein being labeled is an antibody. In addition, many previous methods employ potentially toxic chemicals. Although the pretinning method of Crockford and Rhodes was able to provide a rapid, one-step labeling process yielding approximately 85% of the radionuclide strongly bonded to the protein, the radiochemical purity has not been high enough for clinical application of all monoclonal antibodies, and some products require final purification prior to patient administration. In the present invention, both the optimum conditions for reducing the protein and the optimum conditions for reducing the radionuclide can be achieved while retaining the convenience of one-step labeling. This is achieved by adding steps to the manufacturing process. The protein is reduced with Sn (II) as in the original pretinning method described by Crockford and Rhodes. After reduction is completed, the reduced protein is put through a purification or complexing step to remove excess reducing agent and reaction by-products such as stannic chloride or other Sn (IV) agents. Alternately, an organic reducing agent is used to reduce the protein, the organic reducing agent and reaction products then removed, and Sn (II) is added to form a Sn (II) and sulfur containing protein complex. A Sn (II) radionuclide reducing agent is added to the reduced protein solution in concentrations and with complexing agents which are optimum for subsequent radiolabeling. The reduced protein together with the radionuclide reducing solution are aliquoted, frozen and optionally lyophilized for storage until needed for radiolabeling.

Another alternative is to reduce the antibody using the pretinning method of Crockford and Rhodes disclosed in the '200 patent at optimal concentration of reagents for reducing the protein and forming the Sn (II) and sulfur containing protein complex, and then diluting this solution with reagents to achieve conditions which are optimal for reducing the radionuclide and causing it to transfer to the protein.

SUMMARY OF THE INVENTION (DISCLOSURE OF THE INVENTION)

In accordance with the present invention, a method is provided for radiolabeling proteins with technetium or rhenium in which a reducing agent is used to reduce the disulfide bonds in the protein; excess reducing agent, reaction by-products and any impurities are removed; and, an optimum low concentration and limited amount of pertechnetate or perrhenate reducing agent added to reduce the sodium pertechnetate or perrhenate and facilitate the rapid labeling of the reduced protein by ligand exchange.

In the preferred embodiment, a protein substrate to be radiolabeled is admixed with a solution of Sn (II) chloride composition having a pH of between about 4.5 and about 8.5, and preferably about pH 5.6, the solution further comprising a mixture of sodium potassium tartrate and potassium hydrogen phthalate, the pH adjusted to approximately $5.6\pm0.05$ using sodium hydroxide, and the resulting solution purged of oxygen. Alternatively, the solution may include other salts such as sodium chloride, sodium acetate, gentisic acid, or stannous fluoride. The Sn (II) salt solution is added to the protein in an oxygen free environment, and the protein and Sn (II) salt solution allowed to incubate for several hours (usually twenty-one hours) in the absence of oxygen and at room temperature. Alternately higher or lower incubation temperatures may be used with a corresponding inverse change in the incubation time, such that if the incubation temperature is increased, the incubation time is decreased, and vice versa. For certain proteins, such as some monoclonal antibodies or fragments thereof, the reaction time may be shortened to less than 21 hours to prevent excessive fragmentation of the antibody protein, and can be further reduced if the protein already contains reactive sulfide groups.

Alternatively, the protein may be reduced more rapidly by incubating it with a disulfide group reducing agent, such as dithiothreitol (DTT) in the ratio of 10 mg of DTT per 5 mg of protein per ml of aqueous solution at pH 7.5 to 9.0 for 30 minutes at room temperature. The reducing agent is removed, by purification by any means. This is followed by adding dilute HCl to reduce the pH to $5.6\pm0.05$, and then adding Sn (II) tartrate at pH $5.6\pm0.05$.

Following incubation, the protein and Sn (II) salt solution is either frozen to stop the reduction reaction, or is immediately purified by size exclusion chromatography using an appropriate gel in a column equilibrated with saline. The protein and buffered Sn (II) salt solution is loaded into the column, and eluted using saline, with the molecular weights of the eluant monitored and relevant fractions collected. If necessary, a small amount of Sn (II) solution is added. The fractions corresponding to the protein to be radiolabeled are collected and pooled, and concentrated by ultrafiltration. Alternatively, the protein may be purified by any other suitable method including such methods as dialysis, ultrafiltration, precipitation, preparative high performance liquid chromatography, affinity chromatography, other forms of chromatography or preparative isoelectric focusing. The resulting protein, substantially free of excess Sn (II) salt solution, Sn (IV) salts, contaminants or proteins of molecular weight other than the protein to be radiolabeled, can then be frozen in an oxygen free vial.

To the oxygen free vial containing the frozen purified, reduced and Sn (II) complexed protein, a solution capable of reducing sodium pertechnetate or perrhenate in saline solution is added in a manner to prevent immediate admixing of the two solutions. A pure tin pellet can also be added to each vial. The resulting combination is prepared as layers of frozen solutions or is otherwise prepared without allowing any reaction between the frozen, purified, and reduced protein and the solution for reducing the sodium pertechnetate or perrhenate. A carrier protein may also be added to protect against radiolysis of the purified and reduced protein, and to prevent adhesion of the purified and reduced protein to surfaces, such as the vial wall. A layer of carrier protein, such as non-reduced human serum albumin or another inert diluent such as inositol or another inert sugar, or an amino acid, such as glycine, is added, and the layer is frozen or otherwise prepared without allowing any admixture with the other solutions until use. Oxygen is excluded from the vial containing the two urunixed solutions. The vial is stored frozen or it is lyophilized and stored for subsequent reconstitution when radiolabeling is desired. The solution for reducing the sodium pertechnetate or perrhenate comprises stannous chloride and a mixture of sodium potassium tartrate and potassium hydrogen phthalate, the pH adjusted to approximately 5.6±0.05 using sodium hydroxide, and the resulting solution purged of oxygen. In practice, frequently the same Sn (II) salt solution can be used to reduce both the protein and the sodium pertechnetate or perrhenate; however, the amount or concentration of Sn (II) salts used to reduce sodium pertechnetate or perrhenate is substantially less than the amount or concentration used to reduce the protein. Alternatively, the solution used for reducing sodium pertechnetate or perrhenate can be composed of any substance which effectively reduces sodium pertechnetate or perrhenate and does not alter the protein to be radiolabeled, such as stannous tartrate, stannous phosphonate, stannous gluconate, stannous glucoheptonate, or other substances capable of reducing pertechnetate or perrhenate. The stannous chloride and all such other stannous compounds are referred to in the specification and claims as Sn (II). No more of the pertechnetate or perrhenate reducing solution than is required to reduce the sodium pertechnetate or perrhenate is used. This is done to prevent possible degradation of the protein, primarily by further cleavage of disulfide bonds due to the action of the radionuclide reducing reagent.

Solid, highly pure metallic tin may be added to the vial, generally at or after freezing, and in the form of a non-oxidized tin pellet. The addition of metallic tin prevents oxidation loss during storage and reconstitution.

The resulting frozen or lyophilized combination of purified, reduced, Sn (II) and sulfur containing complexed protein and the radionuclide reducing solution, together with the tin pellet, carrier protein and other inert diluents, are admixed with sodium pertechnetate-Tc-99m or perrhenate solution while avoiding the introduction of oxygen. The admixture is then incubated for a period (usually fifteen minutes) at room temperature to allow for the reduction of the technetium or rhenium and Its binding to the reduced and Sn (II) complexed protein. The admixture may be stabilized by the addition of human serum albumin or other similar protein in normal saline, if a carrier protein was not included in the original vial.

This thus provides a method for radiolabeling proteins containing reactive sulfide groups with radionuelides of technetium or rhenium to obtain stable labeling, by incubating the protein with a first reducing agent to partially reduce the disulfide bonds, purifying the reduced and Sn (II) complexed protein to remove excess first reducing agent and all impurities, and adding only so much of a second reducing agent as is necessary to reduce pertechnetate or perrhenate. A preferred first reducing agent is a source of Sn (II) in a solution composed of a mixture of an alkali metal biphthalate and an alkali metal tartrate having a pH of between about 5.0 and 6.0. The first reducing agent may also be 2-mercaptoethanol, 1,4 dithiothreitol, 2,3 dihydroxybutane-1, 4 dithiol, 2-aminoethanethiol HCl, 2-mereaptoethylamine, thioglycolate, cyanide, cysteine or other substances capable of reducing disulfide bonds, with Sn (II) then added to form an intermediate Sn (II) and sulfur containing complex. A preferred second reducing agent is a source of Sn (II) in a solution composed of a mixture of an alkali metal biphthalate and an alkali metal tartrate having a pH of preferably between about 5.0 and 6.0. The second reducing agent may also be Sn (II) tartrate, Sn (II) gluconate, Sn (II) glucoheptonate, Sn (II) phosphonate, dithionite or other substances capable of reducing pertechnetate or perrhenate. Following the purification of the protein combination, the purified protein combination can be frozen, the second reducing agent added, and the second reducing agent immediately frozen so that no chemical reaction occurs between the purified protein combination and second reducing agent prior to thawing for use. It is also possible, following the freezing of the protein combination and the second reducing agent., to lyophilize the composition. At or subsequent to the addition of the second reducing agent, solid, non-oxidized metallic tin can be added to the combination of the protein combination and the second reducing agent. Purification may be accomplished by passage of the protein combination through a size exclusion chromatography column, or by methods such as use of a desalting column, dialysis, ultrafiltration, precipitation, preparative high performance liquid chromatography, affinity chromatography, or preparative isoelectric focusing. Optimal results are obtained when the concentration of the protein in the protein combination and second reducing agent is at least I milligram per millilater of solution, and the volume of the protein combination and second reducing agent is at least 2 millilaters.

This invention provides for a composition suitable for use in preparing a protein having a stable label of a radionuclide of technetium or rhenium, which composition comprises a protein which has been reduced so that a radionuclide and sulfur containing complex can be formed, so much of a Sn (II)-containing reducing compound for pertechnetate or perrhenate as will reduce the pertechnetate or perrhenate without further reduction of the protein, and optionally pure, non-oxidized metallic tin. The source of pure, non-oxidized metallic tin may be a tin pellet. The composition may be made using a reduced antibody or antibody fragment as the reduced protein. An inert carrier substance may also be added to the composition, such as an inert sugar or non-reduced inert protein. The composition may be lyophilized, preferably buffered at a pH of 4 to 6.

A kit is also provided which includes the frozen or lyophilized combination of purified and Sn (II) and sulfur containing complexed protein and the radionuclide reducing solution in a single oxygen purged vial, together with stabilizing agents, if required, ready for radiolabeling.

Proteins with either monosulfide or disulfide bonds can be radiolabeled with radionuclides such as technetium or rhenium by incubation with a first Sn (II) agent, or other reducing agent, which may be as described above. The period of incubation must be sufficient to allow formation of Sn (II) and sulfur containing complexes. As a result of the formation of the complexes, Sn (IV) reaction by-products, such as stannic chloride, and other impurities, such as protein fragments or polymers, may be formed. A purification step is then employed to substantially remove Sn (IV) and other impurities. A second Sn (11) agent may then be added to the protein containing Sn (11) and sulfur containing complexes, in an amount sufficient to reduce the radionuclide. The radiolabeling is then accomplished by adding the radiolabel, whereby the second Sn (II) agent reduces the radionuclide and the reduced radionuclide forms radionuclide and sulfur containing complexes in the protein.

Radiolabeling may also be accomplished by omitting the step of addition of a second Sn (II) agent, in which case the residual first Sn (II) agent reduces the radionuclide and the reduced radionuclide forms radionuclide and sulfur containing complexes in the protein. This may be accomplished by diluting the reaction mixture after the protein containing Sn (II) and sulfur containing complexes have been formed.

These methods are particularly applicable to technetium-99m in the form of sodium pertechnetate. Both the first and second Sn (II) agents are optimally present in a solution containing alkali metal tartrate at a pH of between 5.0 and 6.0. The second Sn (II) agent can also consist of substances such as stannous glucoheptonate, stannous gluconate, stannous phosphonate, dithionate, or other substances capable of reducing radionuclides.

These methods are particularly applicable to monoclonal antibodies, monoclonal antibody fragments and polyclonal antibodies. These methods can be used to make product, which product on radiolabeling with technetium or rhenium by introduction of sodium pertechnetate or perrhenate and an incubation period, is further characterized by having 85% or more of the technetium or rhenium strongly bonded to the protein. Further, when product is made using monoclonal antibodies or monoclonal antibody fragments, the immunoreactivity of the product is substantially the same as the immunoreactivity of the antibody prior to incubation with the first Sn (II) agent. The product may be lyophilized, and does not require filtration or purification prior to patient in vivo administration.

Proteins with either monosulfide or disulfide bonds may also be radiolabeled with radionuclides such as technetium or rhenium using a modification of the method above. The protein is incubated with a first Sn (II) agent, which may be as described above. The period of incubation must be sufficient to allow formation of Sn (II) and sulfur containing complexes. As a result of the formation of the complexes, Sn (IV) reaction by-products and other impurities may be formed. Sn (IV) reaction by-products can then be complexed with a polyaminocarboxylic acid, such as ethylenediaminetetraacetic acid (EDTA) or diethylenetriaminopentaacetic acid (DTPA). Radiolabeling is accomplished by adding the radionuclide, whereby the residual first Sn (II) agent reduces the radionuclide and the reduced radionuclide forms radionuclide and sulfur containing complexes in the protein.

Radiolabeling may optimally be performed by the addition of a second Sn (II) agent, to facilitate reduction of the radionuclide, following the addition of the complexing agent, such as polyaminocarboxylic acid.

The methods using polyaminocarboxylic acid are particularly applicable to technetium-99m in the form of sodium pertechnetate. Both the first and second Sn (II) agents are optimally present in a solution containing alkali metal tartrate at a pH of between 5.0 and 6.0. The second Sn (II) agent can also consist of substances such as stannous glucoheptonate, stannous gluconate, stannous phosphonate, or other substances capable of reducing radionuclides.

The methods using polyaminocarboxylic acid are particularly applicable to monoclonal antibodies, monoclonal antibody fragments and polyclonal antibodies. These methods can be used to make product, which product on radiolabeling with technetium by introduction of sodium pertechnetate and an incubation period, is further characterized by have 85% or more of the technetium strongly bonded to the protein. Further, when product is made using monoclonal antibodies or monoclonal antibody fragments, the immunoreactivity of the product is substantially the same as the immunoreactivity of the antibody prior to incubation with the first Sn (II) agent. The product may be lyophilized, and does not require filtration or purification prior to patient In vivo administration.

All the foregoing methods result in a proteinaceous composition in which is found a Sn (II) and sulfur containing complex, comprising reactive sulfide groups complexed with Sn (II), and which composition is suitable for radiolabeling with radionuclides such as technetium and rhenium. The composition may also comprise a Sn (II) reducing agent in an amount sufficient to reduce the radionuclide, and may also contain a complexing agent, preferably a polyaminocarboxylic acid such as EDTA or DTPA. The protein may be a monoclonal antibody, monoclonal antibody fragment or polyclonal antibody, and may be made into a product. The product may be lyophilized. On radiolabeling with technetium by introduction of sodium pertechnetate and an incubation period, the product is further characterized by having 85% or more of the technetium strongly bonded to the protein. It is also further characterized by requiring an incubation period of fifteen minutes or less.

Accordingly, it is an object of the present invention to provide a method for direct labeling of proteins with technetium or rhenium, which method will eliminate undesirable fragments or otherwise degraded protein components from the final product.

It is a further object of the present invention to provide a method which results in increased radiolabeling efficiencies utilizing technetium or rhenium as the radioisotope.

It is a further object of the present invention to provide a method to radiolabel antibodies or antibody fragments without loss of affinity of the antibodies or antibody fragments due to the radiolabeling process.

It is a further object of the present invention to provide a method for radiolabeling proteins with technetium or rhenium which does not use potentially toxic or injurious chemicals or substances in the method.

Another object of the present invention is to provide a method and kit which permits radiolabeling to be accomplished by the end user using a single vial, containing both reduced antibody and stannous ions, and further containing a means to maintain low quantities of stannous ions while protecting against oxidation loss, which method requires only a single step to accomplish radiolabeling, being the introduction of sodium pertechnetate.

Other objects, advantages and novel features, and further scope of applicability of the present invention will be set forth in part in the detailed description to follow and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE PREFERRED EMBODIMENTS OF THE INVENTION (BEST MODES FOR CARRYING OUT THE INVENTION)

Any protein, chelating agent or other substrate which contains one or more monosulfide or disulfide bonds which can be reduced can be radiolabeled in accordance with this invention. Representative suitable substrates include human serum albumin, fibrinogen, urokinase, gamma globulin, glycoproteins, other proteins and antibodies, or antibody fragments, of any species, and including both polyclonal and monoclonal antibodies made by any means, as well as chimeric and genetically engineered antibodies, and antibody fragments of all of the foregoing. This includes immunoglobulins of any class, such as IgG, IgM, IgA, IgD, or IgE, of any species origin, including human beings, chimeric antibodies or hybrid antibodies with dual or multiple antigen or epitope specificities, and fragments of all the foregoing, including $F(ab')_2$, $F(ab)_2$, Fab', Fab and other fragments, including hybrid fragments, and further includes any immunoglobulin or any natural, synthetic or genetically engineered protein that functionally acts like an antibody by binding to a specific antigen to form a complex. The term "antibody" or "antibodies", and the phrase "monoclonal antibody component", as used throughout the specification and claims is intended to include all such antibodies and antibody fragments.

The present invention, through inclusion of a purification step, and concomitant removal of excess reducing reagents, presents a number of significant advantages. By removal of all species of reduced protein other than the protein to be radiolabeled, including smaller or larger molecular weight species, competition for reduced Tc-99m is eliminated. This results in significantly higher radiolabeling yields. By keeping the total amount of stannous and stannic ions in the pertechnetate or perrhenate reducing solution as low as possible, the formation of additional reduced protein species is minimized. It generally takes far fewer stannous ions to reduce pertechnetate or perrhenate than to reduce the disulfide bonds in proteins, thereby allowing reduction of pertechnetate or perrhenate without additional reduction of disulfide bonds in the protein to be radiolabeled, which additional reduction could result in protein species other than protein to be radiolabeled.

The present invention also presents significant advantages because it requires only one step to accomplish radiolabeling by the end user, the addition of sodium pertechnetate or perrhenate and the concomitant incubation thereof. This significant simplification is possible because both the stannous ions and the reduced antibody are frozen, together with a carrier protein and other inert diluents, and optionally lyophilized, in the same vial. The addition of the tin pellet, or other source of purified and non-oxidized metallic tin, further preserves the low concentration of stannous ions and helps prevent loss of radiolabel due to oxidation during storage or reconstitution.

The invention is further illustrated by the following non-limiting examples.

EXAMPLE I

A Sn (II) reducing solution was made composed of stannous chloride in a tartrate-phthalate solution. Stannous chloride was prepared by dissolving stannous chloride crystals in concentrated hydrochloric acid at 0.5 M, yielding approximately 94.8 mg of stannous chloride per ml. This solution was then stored in sealed and nitrogen purged vials until used. Alternate sources for stannous chloride can be used, including use of a non-oxidized solid tin pellet contacted with concentrated hydrochloric acid.

A tartrate-phthalate solution of a mixture of sodium potassium tartrate and potassium hydrogen phthalate was prepared. 0.282 g of sodium potassium tartrate was dissolved in 100 ml of distilled water, and to this was added 0.817 g potassium hydrogen phthalate. The pti was adjusted to approximately 5.0, using 10N sodium hydroxide, and was then adjusted to $5.6\pm0.05$ using 1N sodium hydroxide. The resulting solution was stirred and purged of oxygen by bubbling an inert gas, such as nitrogen, helium or the like, through the substance.

The Sn (II) reducing solution was made by measuring a portion of the purged tartrate-phthalate solution into a flask, and slowly adding thereto a volume of the stannous chloride. It is preferable if a stir bar or similar mechanism is used to insure mixture of the stannous chloride as it is added to the solution. Approximately one volume of stannous chloride to 100 volumes of buffer was used. The pH was continuously monitored, and once the stannous chloride was added, the pit was adjusted to approximately 5.0, using 10N sodium hydroxide, and was then adjusted to $5.6\pm0.05$ using 1N sodium hydroxide.

All steps are undertaken in an oxygen free environment, and may be done while bubbling an inert gas through the solution. The resulting solution is purged of oxygen by bubbling an inert gas, such as nitrogen, helium or the like, through the substance.

Alternately, the antibody reducing solution can be made using other disulfide reducing agents such as 2-mercaptoethanol, 1,4 dithiothreitol, 2,3 dihydroxybutane-1, 4 dithiol, 2-aminoethanethiol HCl, 2-mercaptoethylamine, thioglycolate, cyanide, cysteine, or other disulfide splitting reagents.

The protein to be reduced is placed in a nitrogen purged, sealed vial. If monoclonal antibody or fragments thereof are to be labeled, a minimum of 0.1 mg, and preferably at least 2 mg, of monoclonal antibody or fragments is used, at a concentration of I mg or more per ml, preferable 1.7 mg/ml. The monoclonal antibody, fragments or other protein may be diluted in normal saline, or concentrated by ultrafiltration, as may be necessary. To the protein, Sn (II) reducing solution is added, in the approximate ratio of 3 volumes of protein to 2 volumes of Sn (II) reducing solution. The vial containing the protein and Sn (II) reducing solution is then allowed to incubate, preferably in an oxygen free environment, such as a container filled with nitrogen or another inert gas. The vial is allowed to incubate at room temperature for a period sufficient to allow reduction of the disulfide bonds in the protein. Generally, incubation for between one and twenty-four hours at room temperature is adequate, with incubation for twenty-one hours at room temperature being preferred for most whole immunoglobulins. If the temperature is increased, the incubation time is decreased, and conversely, incubation at lower temperatures requires correspondingly longer incubation times. Incubation is terminated by freezing the admixture of protein and Sn (II) reducing solution by dilution or by proceeding immediately to purification.

When other reducing agents are used; such as 2-mercaptoethanol, 1,4 dithiothreitol, 2,3 dihydroxybutane- 1,4 dithiol, 2-aminoethanethiol HCl, 2-mercaptoethylamine, thioglycolate, cyanide, cysteine, or other disulfide splitting reagents, the incubation time must be adjusted for the specific reducing agent being used. Generally, a shorter incubation time is required. After the reducing solution is removed, Sn (II) salt is added to form a Sn (II) and sulfur containing complex, and thus preserve the reduced disulfide groups during subsequent purification steps. The purification steps undertaken with these reducing agents must remove substantially all of the reducing agent.

The admixture of protein and Sn (II) reducing or other reducing solution is purified, preferably by size exclusion chromatography. A column is packed with an appropriate gel, such as Sephacryl-200 gel (Pharmacia, Piscataway, N.J.) for use with low molecular weight monoclonal antibody F(ab')$_2$ fragments. The column is equilibrated with an appropriate elution buffer, such as gentisate buffered saline. The admixture of protein and reducing solution is applied to the column and fractionated, using the elution buffer. A fraction profile is generated using an ultraviolet detector or similar device, and the fractions containing the resulting protein to be radiolabeled are collected and pooled. The resulting reduced protein is concentrated, if necessary, preferably to a concentration of 1.7 mg/ml. Concentration can be accomplished by ultrafiltration. The resulting concentrate can also be dialyzed against normal saline to remove any residual Sn (IV) salts or other residual reducing agent.

Alternately, the admixture of Sn (II) and sulfur containing complexed protein and Sn (II) or other reducing solution may be purified by passage of the admixture through a desalting column, collecting the reduced protein and discarding the Sn (IV) salts and excess reducing reagents. The resulting eluant can be concentrated and dialyzed as required. This method will remove excess Sn (11) solution, Sn (IV) reaction by-product and other reducing reagents, but will not necessarily remove other impurities, such as smaller fragments of the protein resulting from over reduction of the disulfide bonds in the protein or aggregation of reduced proteins. These small fragments or large aggregates, in the case of monoclonal antibodies, may not be immunoreactive, or may have a biodistribution different than than of the desired protein, necessitating their removal from the final product.

Alternately, the admixture of reduced protein and Sn (II) or other reducing solution may also be purified by other means, including dialysis, ultrafiltration, precipitation, preparative high performance liquid chromatography, affinity chromatography, other forms of chromatography, preparative isoelectric focusing, and other purification means common to the art.

The purified, reduced and Sn (II) complexed protein is then purged of oxygen, preferably by bubbling an inert gas such as nitrogen through the solution, and can be frozen in oxygen-purged vials. To each vial containing frozen protein solution, pertechnetate reducing solution is added, and the contents either immediately frozen or lyophilized, so that no reaction takes place between the frozen protein solution and the pertechnetate reducing solution. A non-oxidized tin pellet may also be added to the vial, which tin pellet will replace trace amounts of Sn (II) and help to stabilize the low concentration of stannous ions in the pertechnetate reducing solution, and to help prevent losses of radiolabel due to reoxidation during storage of the radiolabeled product. The pertechnetate reducing solution can be made as the Sn (II) reducing solution was made, except that approximately one volume of stannous chloride at 0.5M is added to approximately 5,000 volumes of tartrate-phthalate solution, resulting in a pertechnetate reducing solution of approximately 0.1 millimolar. Approximately one volume of pertechnetate reducing solution is added to two volumes of purified, reduced and Sn (II) complexed protein. Optimally, the protein solution is at a concentration of approximately 1.7 mg/ml, and to each 1.32 ml of the purified, reduced and Sn (II) complexed protein solution, approximately 0.68 ml of pertechnetate reducing solution is added.

Alternately, the pertechnetate reducing solution can be made using Sn (II) glucoheptonate, Sn (II) tartrate, Sn (II) phosphonate, dithionite and other commonly used Tc-99m radiopharmaceutical kits.

The pertechnetate reducing solution can also be used to reduce perrhenate. The discussion of pertechnetate and pertechnetate compounds throughout the specification is also applicable to perrhenate and perrhenate compounds. Likewise, the discussion throughout the specification of technetium and its compounds is applicable to rhenium and its compounds.

To radiolabel, the desired activity of sodium pertecbnetate-Te-99m is added and admixed, and the admixture allowed to incubate for a period, generally approximately fifteen minutes. This step is conducted while avoiding or minimizing the introduction of atmospheric oxygen. If desired, the resultant radiolabeled protein can be stabilized by the addition of 1% human serum albumin in normal saline or other suitable protective protein.

The source of technetium-99m is conventionally obtained as sodium pertechnetate-Tc-99m from a 99Mo/99mTc generator. Any source of pharmaceutically acceptable technetium-99m may be utilized in the present invention.

Alternatively other radioisotopes of technetium and isotopes of rhenium such as Re-186 and Re-188 may be used. When perrhenate rather than pertechnetate is reduced, usually a higher temperature and a longer radiolabeling time are required to carry the reaction to completion.

EXAMPLE II

This example illustrates the process of this invention for labeling immunoglobulin C (IgG). IgG is obtained obtained from animals such as sheep, goats, mice or humans. Sodium Pertechnetate-Tc-99m U.S.P. is obtained from any commercial source.

A Sn (II) disulfide bond reducing agent was prepared by adding 0.2 ml of 0.5 M stannous chloride in concentrated HCl (12 M) to 20 ml of a 40 mM potassium biphthalate and 10 mm sodium tartrate solution (pH of 5.6). The stannous chloride was prepared by adding the concentrated hydrochloric acid to non-oxidized pellets of SnCl$_2$ having a surface free of dull stannous oxide. The pH of the resultant reducing solution then was brought up to 5.6±0.05, by adding 10 M NaOH to a pH of 5.5, and adding 1 M NAOH to adjust to the final pH.

An IgG preparation was made by diluting 0.25 ml of Immune Globulin (Human), U.S.P., Cutter Biological, which contained 15-18% protein stabilized with 0.21-0.32 M glycine, with 7.25 mi of Sterile Water for Injection, U.S.P., and filtering through a 0.22 micron filter. 5 ml of the Sn (II) reducing solution was mixed with 7.5 ml of the IgG preparation. The vial containing the admixed solutions was sealed and flushed with $N_2$ gas to remove oxygen. This admixed solution was stored for 21 hours at room temperature in the dark to allow for the partial reduction of disulfide bonds to form what is referred to subsequently as reduced protein. After the 21 hour incubation the contents of the vial was passed through a PD-10 desalting column (Pharmacia LKB Biotechnology, Piscataway, N.J.); the protein containing fraction was collected and the remaining eluate, which contained the Sn (II), Sn (IV) and other salts, was discarded. The reduced and Sn (II) complexed protein fraction was concentrated by ultrafiltration to a concentration of 1.7 mg/ml. 0.5 mg aliquots of reduced and Sn (II) complexed protein were placed in sealed, $N_2$ gas filled serum vials and frozen. A Sn (II) pertechnetate reducing solution was made of 0.5 ml of 0.1 Mm $SnCl_2$ in 40 mM potassium biphthalate/10 mM sodium at a pH of 5.6. The Sn (11) pertechnetate reducing solution was added without allowing the reduced antibody solution to thaw, and this solution was also frozen. A sterile, 3 mm diameter tin metal shot was added, the vial flushed with $N_2$ and stored at $-20°$ C. until needed for radiolabeling.

To radiolabel the gamma globulin preparation with Tc-99m, 1.0 ml of Sodium Pertechnetate-Tc-99m, U.S.P., containing 2.5 mCi of radioactivity, was added to the vial, and the vial and contents brought to room temperature, mixed and allowed to stand for 15 minutes. Thin layer chromatographic analysis of the product revealed that 99.6% of the radioactivity was protein bound. High performance liquid chromatography, using both UV and radioisotope detectors, showed that the Tc-99m elution paralleled the protein elution profile.

EXAMPLE III

This example illustrates the process of this invention for labeling monoclonal murine antibodies of IgG and IgM classes. The antibody was obtained from murine ascites or bioreactor fluid, purified to greater than 95%, and prepared at concentrations of greater than 1 mg/ml in 0.9% NaCl solution.

A Sn (II) reducing solution was prepared as in Example II. Two whole antibody preparations were tested; B72.3, an IgG murine antibody, and anti-SSEA-1, an IgM murine antibody. Each antibody preparation was at a protein concentration of 1.7 mg/ml. To each ml of purified protein solution was added 0.66 ml of Sn (II) reducing solution. The admixed solutions were incubated and passed through a PD-10 column as in Example II. The reduced protein fraction was concentrated by ultrafiltration to a concentration of 2 mg/ml. Aliquots of reduced protein, containing from 0.5 to 2.0 mg protein, were placed in sealed, $N_2$ gas filled serum vials and frozen.

A pertechnetate reducing solution was prepared by dissolving 50 mg of gentisic acid, 0.375 $\mu$g $SnCl_2$ and 975 $\mu$g of sodium potassium tartrate in 50 ml of distilled water which had previously been deoxygenated by bubbling $N_2$ gas through it for two to three minutes. The pH was adjusted to 7.0 by addition of very dilute (0.05 N) NAOH. Equal volumes of this solution were layered over the frozen, reduced and Sn (II) complexed protein solution and this solution frozen. A sterile, 3mm diameter tin metal shot was added, the vial flushed with $N_2$ and stored at $-20°$ C. until needed for radiolabeling.

To radiolabel the IgG or IgM preparations with Tc-99m, 1.0 ml of Sodium Pertechnetate-Tc-99m, U.S.P., containing 2.5 mCi of radioactivity, was added to each vial, and the vial and contents brought to room temperature, mixed and allowed to stand for 15 minutes. Thin layer chromatographic analysis of the products revealed that 90.0% to 96.5% of the radioactivity was protein bound. High performance liquid chromatography (HPLC), using both UV and radioisotope detectors, showed that the Tc-99m elution paralleled the protein elution profile. No non-protein bound radioactivity was found by HPLC analysis.

EXAMPLE IV

This example illustrates the process of this invention for labeling F(ab')$_2$ fragment of a monoclonal antibody. This example also shows that the composition of the radiolabeled product varies with the method and type of disulfide reducing reagent used. This example also shows that the current method is superior to the original direct labeling method of Crockford and Rhodes, U.S. Pat. No. 4,424,200 entitled "METHOD FOR RADIOIABELING PROTEINS WITH TECHNETIUM -99M", for this particular monoclonal antibody fragment. The F(ab')$_2$ fragment was obtained by pepsin digestion of murine monoclonal antibody followed by chromatographic purification which separated the F(ab')$_2$ fragments from other materials found in the pepsin digest with greater than 95% purity.

The monoclonal antibody fragment used in this example was obtained from Sorin Biotechnics, Italy. It was a murine anti-CEA F(ab')$_2$ which previous experimentation had shown very poor radiolabeling with Tc-99m using the pretinning method.

Four different radiolabeling procedures were employed; one used the original pretinning method described in U.S. Pat. No. 4,424,200, and the other three procedures used methods taught in this invention. The four procedures can be summarized as follows:

1. The original pretinning method described in U.S. Pat. No. 4,424,200, in which a Sn (II) reducing solution was prepared as described in Example II, but no purification step was employed, and no pertechnetate reducing solution was added.

2. The method of this invention using Sn (II) reducing solution to reduce disulfide bonds in the antibody fragment, as described in Example II, including a purification step using a PD-10 desalting column, and a pertechnetate reducing solution composed of stannous salt with a tin pellet.

3. The method of this invention using 2-mercaptoethanol to reduce disulfide bonds in the antibody fragment. A 5% solution of 2-mereaptoethanol was prepared in 0.1 M phosphate buffer at pH 8.0. One ml of this solution was added to 1 mg of the lyophilized antibody fragment protein and mixed to dissolve. After 1 hour incubation at room temperature, 1.6 ml of saline was added and the partially reduced protein separated from the other components in the solution by passage through a PD-10 desalting column. The protein was concentrated by ultrafiltration to 1.7 mg/ml. A pertechnetate reducing solution composed of stannous salt with a tin pellet, as described in Example II, was then applied.

4. The method of this invention using dithiothreitol to reduce disulfide bonds in the antibody fragment. 15.4 mg of dl-dithiothreitol (DTT) was dissolved in 10 ml of a solution of 50 mM Tris and 1 mM EDTA at pH 8.0. For each mg of lyophilized protein to be reduced, 0.33 ml of the reducing solution was added with mixing to dissolve the protein. The reduction mixture was allow to react at 37° C. for one hour. The partially reduced protein was purified by size exclusion column chromatography with collection of the protein fraction corresponding to the molecular weight of the original F(ab')$_2$ antibody fragment. The chromatographically purified fragment was concentrated to 1.7 mg/ml in 0.9% saline by ultrafiltration. A pertechnetate reducing solution composed of stannous salt with a tin pellet, as described in Example II, was then applied.

For each of the four preparations, the frozen and vialed antibody fragment was radiolabeled and tested as described in Example II. The results of the four different procedures utilizing the same antibody fragment are listed in Table 1.

Table 1 shows that this specific F(ab')$_2$ murine monoclonal antibody fragment effectively fails to radiolabel using the original pretinning method taught in U.S. Pat. No. 4,424,200, in which there is no purification step and no addition of limited amounts of pertechnetate reducing solution, yet effectively radiolabels using methods of this invention, particularly when an agent other than Sn (II) was used to reduce the disulfide bonds. The same pertechnetate reducing agent, here Sn (II), was used in each procedure. Conditions were not optimized during the procedure to obtain greater than 85% binding. The purpose of the comparison was to show how the binding can be grossly improved by using the process of the invention.

TABLE I

COMPARISON OF RESULTS USING DIFFERENT METHODS FOR PARTIAL REDUCTION OF THE DISULFIDE BONDS OF ANTI-CEA F(ab')$_2$

| Disulfide Reduction Method | Results |
| --- | --- |
| 1. Original pretinning U.S. Pat. No. 4,424,200 method | 4-9% of the Tc-99m bound to F(ab')$_2$; 45-53% bound to smaller fragments. |
| 2. This invention using Sn (II) | 18-29% of the Tc-99m bound to F(ab')$_2$; 51-76% bound to smaller fragments. |
| 3. This invention using 2-mercaptoethanol | 79% of the Tc-99m bound to F(ab')$_2$; none bound to smaller fragments. |
| 4. This invention using DTT | 74% of the Tc-99m bound to F(ab')$_2$; none bound to smaller fragments |

EXAMPLE V

This example illustrates the process of this invention for labeling a monoclonal antibody which cannot be satisfactorily labeled by the original direct or pretinning method, or by other equivalent direct labeling methods. The reason for the failure of the previous direct methods with certain monoclonal antibodies is that during the reduction of the antibody either fragmentation or aggregation of the antibody occurs which results in protein species of altered molecular weight. An example of this is an anti-CEA murine monoclonal IgG provided by Sorin Biomedia, Italy. When this antibody is reduced with Sn (II) salts, small amounts of fragments are formed which label preferentially with the reduced Tc-99m. When this antibody is reduced with dithiothreitol or 2-mercaptoethanol, dimers and polymers of reduced IgG are formed which label with Tc-99m. By the method of this invention, the antibody, after the disulfide bond reduction step, is purified by passage through a size exclusion chromatograph column. The column eluate corresponding only to the molecular weight of the original antibody was separated from both the smaller or larger protein species. A quantity of pertechnetate reducing solution sufficient to reduce the sodium pertechnetate but not to further reduce disulfide bonds in the antibody was added, and the antibody radiolabeled. The resulting Tc-99m labeled protein was of the correct molecular weight and free of the smaller or larger molecular weight contaminants.

EXAMPLE VI

This example illustrates the use of purification and EDTA to obtain higher HPLC yields.

Four aliquots of a chimeric IgG monoclonal antibody were reduced with a Sn (II) reducing agent as in Example II. Two aliquots were purified by passage through a PD-10 column, followed by addition of Sn (II) pertechnetate reducing solution. The remaining two aliquots were not purified, and no additional Sn (II) pertechnetate reducing solution was added. To one of each of the two pairs of aliquots, ethylenediaminetetraacetic acid (EDTA) was added prior to radiolabeling.

Quantitative radiochemical purity was determined by HPLC yield. In this method, the percent of strongly bonded Tc-99m is determined as the percent of Tc-99m recovered in HPLC size exclusion chromatography of the total Tc-99m injected multiplied by the percent of Tc-99m under the IgM protein peak. Weakly bonded Tc-99m is almost completely transferred and bound to the HPLC column, with unreduced Tc-99m elutes, but not with the protein peak. This method thus provides a measure of strongly bonded Tc-99m.

TABLE 2

COMPARISON OF RESULTS USING EDTA TO PARTIALLY BIND IMPURITIES

| Reduction Method | HPLC Yield |
| --- | --- |
| 1. SN (II) reduction, no purification | 52% |
| 2. SN (II) reduction, no purification, EDTA | 78% |
| 3. SN (II) reduction, PD-10 desalting column, SN (II) pertechnetate reducing solution | 96% |
| 4. SN (II) reduction, PD-10 desalting column, SN (II) pertechnetate reducing solution, EDTA | 97% |

EXAMPLE VII

This example illustrates the formation of reactive sulfide groups on reduction of disulfide bonds by Sn (II) and by dithiothreitol (DTT). Murine monoclonal IgM antibody was labeled with I-125 using the Iodobead method. Aliquots were incubated with Sn (II) reducing solution made as in Example II; the aliquots were removed at different time intervals, up to 21 hours, and passed through a PD-10 column to stop the reduction reaction. Aliquots were also incubated with DTT. Sodium chloride was used as a control. The PD-10 columns were eluted with nitrogen purged saline to prevent reoxidation of reactive sulfide groups. One portion of each aliquot was used for measurement of free reactive sulfide groups and the other portion was used for Tc-99m labeling and the measurement of the percent of strongly bonded Tc-99m.

Reactive sulfide group formation was determined by relative binding of the I-125 labeled antibody to Thio Avidgel F (Bioprobe, Justin, Calif.). Thio Avidgel F binds proteins which have free sulfhydryl or reactive sulfide groups; if such groups are formed during incubation with reducing agents, then the percent antibody binding should be proportional to reactive sulfide groups. Tc-99m labeling was accomplished by using a Sn (II) pertechnetate reducing solution, prepared as in Example II, to which was added human serum albumin and inositol. The percent strongly bonded Tc-99m was determined by HPLC yield as described in Example VI.

TABLE 3

SULFHYDRYL GROUP CORRELATION TO STRONGLY BONDED Tc-99m

| Reducing Agent | Incubation Time (Hours) | Percent Binding To Thiogel | HPLC Yield |
|---|---|---|---|
| NaCl | NA | 10% | 5.1% |
| Sn (II) | 1 | 14% | 20.9% |
| SN (II) | 21 | 23% | 46.7% |
| DTT | 1 | 62% | 57.8% |

EXAMPLE VIII

This example illustrates that the process of this invention, using the Sn (II) reducing agent of Example II followed by passage through a PD-10 column, does not affect the immunoreactivity of monoclonal antibodies. F(ab')2 antibody specific for myosin was spiked with I-125 labeled polyclonal immune globulin. A portion was reduced as described and passed through a PD-10 column. Aliquots of both the reduced F(ab')2 and unreduced F(ab')2 were then adjusted to yield the same concentration using the 1-125 labeled polyclonal immune globulin as the standard. ELISA was performed against purified heavy chain myosin antigen with both aliquots using decreasing concentrations of the F(ab')2 antibody. The affinity constants were calculated at one-half plateau maximum absorbance, and were found to be identical.

The preceding examples can be repeated with similar success by substituting the generically or specifically described reactants and/or operating conditions of this invention for those used in the preceding examples. In particular, other proteins, chelating agents or substrates which contain monosulfide or disulfide bonds which can be reduced may be used in place of IgC, IgM and F(ab')2 monoclonal antibody; other reducing agents can be used to reduce the disulfide bonds in the substance to be radiolabeled; other purification methods can be used to remove the reducing agent; other pertechnetate reducing agents can be used to reduce the sodium pertechnetate; and isotopes of rhenium can be used in addition to isotopes of technetium. The foregoing are merely illustrative, and other equivalent embodiments are possible and contemplated.

Although the invention has been described with reference to these preferred embodiments, other embodiments can achieve the same results. Variations and modifications of the present invention will be obvious to those skilled in the art and it is intended to cover in the appended claims all such modifications and equivalents.

What is claimed is:

1. A method of radiolabeling a substrate containing one or more monosulfides or disulfide bonds with a radionuclide to obtain stable labeling, comprising the steps of:
    a) incubating the substrate containing one or more monosulfides or disulfide bonds with a first Sn (II) agent, the period of incubation being sufficient to allow formation of Sn (II)-containing and sulfur-containing complexes, while preventing excessive fragmentation of the substrate;
    b) purifying the reduced substrate to substantially remove uncomplexed Sn (II) agents and other impurities;
    c) adding a second Sn (II) agent to the purified substrate with Sn (II)-containing and sulfur-containing complexes in a sufficient amount to reduce the radionuclide yet not generate significant radiochemical impurities, the radionuclide to be added in a subsequent step; and
    d) radiolabeling the purified substrate with the Sn (II)-containing and sulfur-containing complexes by adding the radionuclide, whereby the Sn (II) agents reduce the radionuclide and the reduced radionuclide forms radionuclide-containing and sulfur-containing complexes.

2. The method of claim 1 wherein the source of Sn (II) agent is present in a solution comprising alkali metal tartrate having a pH of between approximately 5.0 and 6.0.

3. The method of claim 1 wherein the source of Sn (II) agent comprises a member selected from the group consisting of stannous tartrate, stannous glucoheptonate, stannous gluconate, stannous phosphonate, stannous chloride, and stannous fluoride.

4. The method of claim 1 wherein the radionuclide comprises a member selected from the group consisting of technetium and rhenium.

5. The method of claim 4 wherein the radionuclide is technetium-99m in the form of sodium pertechnetate.

6. The method of claim 1 wherein following step c), and prior to step d), the purified substrate with Sn (II)-containing and sulfur-containing complexes and second Sn (II) agent are frozen in a vial, whereby the frozen purified substrate with Sn (II)-containing and sulfur-containing complexes and second Sn (II) agent can be maintained for an indefinite period before radiolabeling in step d) by the addition of the radionuclide to the vial.

7. The method of claim 1 wherein following step c), and prior to step d), the purified substrate with Sn (II)-containing and sulfur-containing complexes and second Sn (II) agent are lyophilized in a vial, whereby the lyophilized purified substrate with Sn (II)-containing and sulfur-containing complexes and second Sn (II) agent can be maintained for an indefinite period before radiolabeling in step d) by the addition of the radionuclide to the vial.

8. The method of claim 1 wherein 85 percent or more of the radionuclide is strongly bonded to the substrate.

9. The method of claim 1 wherein the substrate comprises a member selected from the group consisting of chelating agents and proteins.

10. A method of radiolabeling a substrate containing one or more monosulfides or disulfide bonds with a radionuclide to obtain stable labeling, comprising the steps of:
    a) incubating the substrate containing one or more monosulfides or disulfide bonds with a first Sn (II) agent, the period of incubation being sufficient to allow formation of Sn (II)-containing and sulfur-containing complexes, while preventing excessive fragmentation of the substrate;
    b) purifying the reduced substrate to remove uncomplexed Sn (II) agents and other impurities yet retaining Sn (II) in a sufficient amount to reduce the radionuclide and not generate significant radiochemical impurities, the radionuclide to be added in a subsequent step; and c) radiolabeling in a single vial the purified substrate with the Sn (II)-containing and sulfur-containing complexes by adding the radionuclide, whereby the Sn (II) agent reduces the radionuclide and the reduced radionuclide and substrate form radionuclide-containing and sulfur-containing complexes.

11. The method of claim 10 wherein the source of Sn (II) agent is present in a solution comprising alkali metal tartrate having a pH of between approximately 5.0 and 6.0.

12. The method of claim 10 wherein the source of Sn (II) agent comprises a member selected from the group consisting of stannous tartrate, stannous glucoheptonate, stannous gluconate, stannous phosphonate, stannous chloride, and stannous fluoride.

13. The method of claim 10 wherein the radionuclide comprises a member selected from the group consisting of technetium and rhenium.

14. The method of claim 13 wherein the radionuclide is technetium-99m in the form of sodium pertechnetate.

15. The method of claim 10 wherein following step b), and prior to step c), the purified substrate with Sn (II)-containing and sulfur-containing complexes is frozen in a vial, whereby the frozen purified substrate with Sn (II)-containing and sulfur-containing complexes can be maintained for an indefinite period before radiolabeling in step c) by the addition of the radionuclide to the vial.

16. The method of claim 10 wherein following step b), and prior to step c), the purified substrate with Sn (II)-containing and sulfur-containing complexes is lyophilized in a vial, whereby the lyophilized purified substrate with Sn (II)-containing and sulfur-containing complexes can be maintained for an indefinite period before radiolabeling in step c) by the addition of the radionuclide to the vial.

17. The method of claim 10 wherein 85 percent or more of the radionuclide is strongly bonded to the substrate.

18. The method of claim 10 wherein the substrate comprises a member selected from the group consisting of chelating agents and proteins.

19. A method of radiolabeling a substrate containing one or more monosulfides or disulfide bonds with a radionuclide to obtain stable labeling, comprising the steps of:
a) incubating the substrate containing one or more monosulfides or disulfide bonds with a first Sn (II) agent, the period of incubation being sufficient to allow formation of Sn (II)-containing and sulfur-containing complexes, while preventing excessive fragmentation of the substrate;
b) complexing the free Sn (II) agents with a complexing agent so as not to further reduce the substrate, while retaining complexed Sn (II) agents for reducing the radionuclide, the radionuclide to be added in a subsequent step; and
c) radiolabeling in a single vial the substrate with the Sn (II)-containing and sulfur-containing complexes by adding the radionuclide, whereby the complexed Sn (II) agents reduce the radionuclide and the reduced radionuclide and substrate form radionuclide-containing and sulfur-containing complexes.

20. The method of claim 19 wherein the source of Sn (II) agent is present in a solution comprising alkali metal tartrate having a pH of between approximately 5.0 and 6.0.

21. The method of claim 19 wherein the source of Sn (II) agent comprises a member selected from the group consisting of stannous tartrate, stannous glucoheptonate, stannous gluconate, stannous phosphonate, stannous chloride, and stannous fluoride.

22. The method of claim 19 wherein the radionuclide comprises a member selected from the group consisting of technetium and rhenium.

23. The method of claim 22 wherein the radionuclide is technetium-99m in the form of sodium pertechnetate.

24. The method of claim 19 wherein following step b) a second Sn (II) agent is added to the combination of the complexing agent and substrate with Sn (II)-containing and sulfur-containing complexes in a sufficient amount to completely reduce the radionuclide, whereby the reduced radionuclide forms radionuclide-containing and sulfur-containing complexes.

25. The method of claim 24 wherein following the addition of the second Sn (II) agent and prior to radiolabeling, the free Sn (II) complexes, second Sn (II) agent, and substrate with Sn (II)-containing and sulfur-containing complexes are frozen in a vial, whereby the frozen free Sn (II) complexes, second Sn (II) agent, and substrate with Sn (II)-containing and sulfur-containing complexes can be maintained for an indefinite period before radiolabeling by the addition of the radionuclide to the vial.

26. The method of claim 24 wherein following the addition of the second Sn (II) agent and prior to radiolabeling, the free Sn (II) complexes, second Sn (II) agent, and substrate with Sn (II)-containing and sulfur-containing complexes are lyophilized in a vial, whereby the lyophilized free Sn (II) complexes, second Sn (II) agent, and substrate with Sn (II)-containing and sulfur-containing complexes can be maintained for an indefinite period before radiolabeling by the addition of the radionuclide to the vial.

27. The method of claim 19 wherein following step b), and prior to step c), the free Sn (II) complexes and substrate with Sn (II)-containing and sulfur-containing complexes are frozen in a vial, whereby the frozen free Sn (II) complexes and substrate with Sn (II)-containing and sulfur-containing complexes can be maintained for an indefinite period before radiolabeling in step c) by the addition of the radionuclide to the vial.

28. The method of claim 19 wherein following step b), and prior to step c), the free Sn (II) complexes and substrate with Sn (II)-containing and sulfur-containing complexes are lyophilized in a vial, whereby the lyophilized free Sn (II) complexes and substrate with Sn (II)-containing and sulfur-containing complexes can be maintained for an indefinite period before radiolabeling in step c) by the addition of the radionuclide to the vial.

29. The method of claim 19 wherein 85 percent or more of the radionuclide is strongly bonded to the substrate.

30. The method of claim 19 wherein the complexing agent is a polyaminocarboxylic acid.

31. The method of claim 29 wherein the polyaminocarboxylic acid comprises at least one member selected from the group consisting of EDTA and DTPA.

32. The method of claim 19 wherein the substrate comprises a member selected from the group consisting of chelating agents and proteins.

* * * * *